Figure 1:
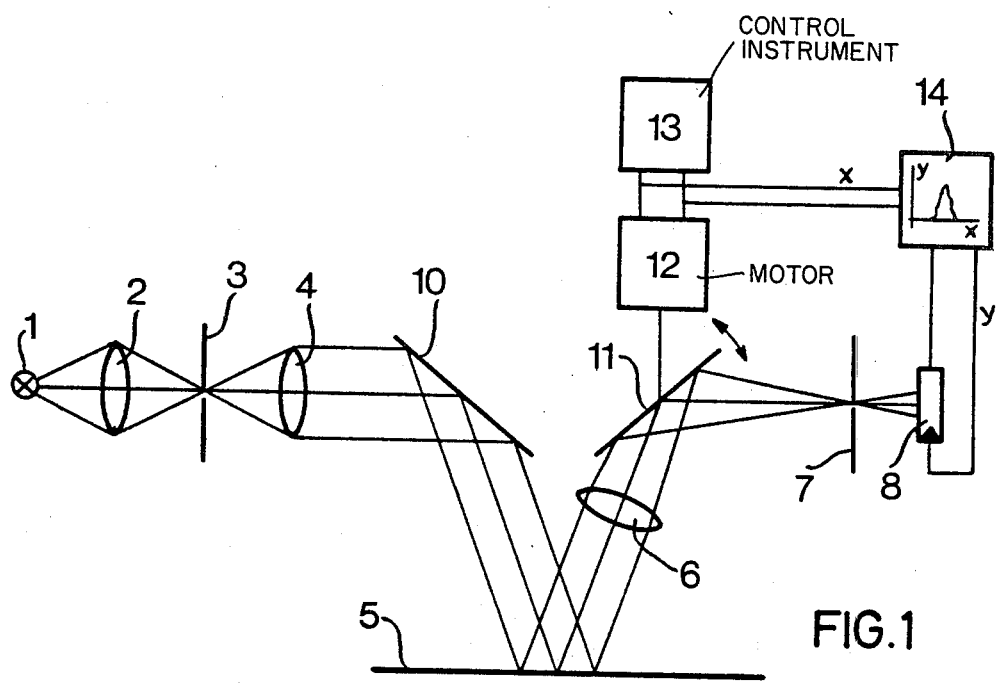

United States Patent [19]

Lamprecht et al.

[11] 4,285,597
[45] Aug. 25, 1981

[54] GONIOPHOTOMETER FOR MEASURING THE GLOSS AND/OR LIGHT DIFFUSION OF SURFACES

[75] Inventors: Josef Lamprecht, Ludwigshafen; Gregor Ley, Wattenheim, both of Fed. Rep. of Germany

[73] Assignee: BASF Aktiengesellschaft, Ludwigshafen, Fed. Rep. of Germany

[21] Appl. No.: 154,892

[22] Filed: May 30, 1980

[30] Foreign Application Priority Data

Jun. 15, 1979 [DE] Fed. Rep. of Germany ....... 2924241

[51] Int. Cl.³ .......................................... G01N 21/47
[52] U.S. Cl. .................................... 356/446; 250/234; 350/486
[58] Field of Search ...................... 356/445, 446, 329; 250/234; 350/6.1, 6.5, 486

[56] References Cited

FOREIGN PATENT DOCUMENTS 2402127 7/1975 Fed. Rep. of Germany .
2556150 7/1975 Fed. Rep. of Germany .

Primary Examiner—John K. Corbin
Assistant Examiner—Bruce Y. Arnold
Attorney, Agent, or Firm—Keil & Witherspoon

[57] ABSTRACT

An improved goniophotometer for determining the gloss and/or haze of a surface is disclosed. The device comprises a light source, one or more convex lenses for illuminating the surface, a field stop in the image plane of the light source, a light detector, and a rotatably mounted mirror located between the surface and the field stop. Whereas prior art goniophotometers translated the field stop through the reflected beam in order to measure the beam profile, such an arrangement required an additional positive lens placed after the field stop for uniform illumination of the (fixed) light detector in order to avoid errors in measurement resulting from locally varying sensitivity of the detector. By using a rotationally scanned mirror before the field stop, the need for means to translate the field stop as well as the need for the additional positive lens is made unnecessary.

2 Claims, 2 Drawing Figures

GONIOPHOTOMETER FOR MEASURING THE GLOSS AND/OR LIGHT DIFFUSION OF SURFACES

The present invention relates to a goniophotometer for determining the gloss and/or haze of surfaces, comprising a light source, one or more convex lenses for illuminating the surface, a field stop in the image plane of the light source, and a light detector.

German Published Application DAS No. 2,556,150 discloses an apparatus for measuring the reflectance of plane surfaces, in which the field stop is movable at right angles to the direction of reflection, in order to record the angular intensity distribution of the light emanating from the surface, the measuring optics being fixed in the direction of reflection. With this arrangement, an additional lens is required for uniform illumination of the light detector, in order to avoid errors in measurement resulting from locally varying light sensitivity of the detector.

Further, German Published Application DAS No. 2,402,127 discloses an apparatus for measuring the light diffusion of surfaces in which the light scattered at a certain angle, differing from the direction of reflection, falls, through a ring-shaped field stop in the plane of the image of the light source, onto a second light detector. A disadvantage of this arrangement is that two different detectors are used, and it is possible that these may have different light sensitivities.

It is an object of the present invention to provide a low-cost apparatus which is simple to operate and by means of which the angular distribution of the scattered light, or certain points of the distribution curve, can be determined, or recorded, in a short time.

According to the invention, this object is achieved if a rotatably mounted mirror is located between the specimen surface and the field stop.

Advantageously, the mirror is moved by a motor, especially a scanner motor or stepping motor. The advantage achieved by means of the invention is that apart from the rotatably mounted mirror no moving components are required, and that the light detector is uniformly illuminated. The entire optics can be mounted in a simple manner on an optical axis.

Figure 2:
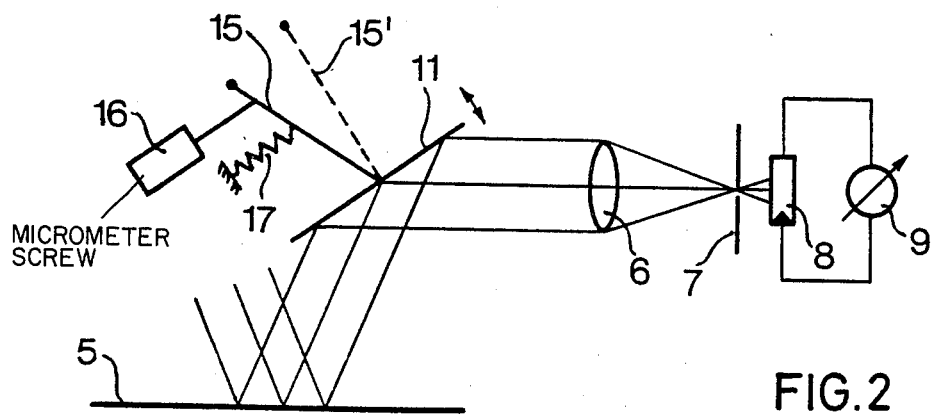

The invention is described in more detail below with the aid of the accompanying drawing in which FIG. 1 shows a goniophotometer with motor-driven mirror and FIG. 2 shows a goniophotometer in which only two angular positions of the mirror are provided.

A beam is produced by a light source 1, and is rendered parallel by convex lenses 2, 4 and field stop 3 and is projected, via a fixed deflecting mirror 10, onto the surface 5 which is to be measured. The light emanating from the surface 5 and consisting of reflected light and scattered light is gathered by a convex lens 6, which may be located in front of, or behind, a rotatably mounted mirror 11, and impinges, through a fixed field stop 7, on a light detector 8. The mirror 11 is driven by a motor 12 which in turn is set by a control instrument 13. The signal x corresponding to the position of the mirror 11, and the signal y, corresponding to the amount of light passing through field stop 7, are recorded by an x, y pen recorder 14.

In a second embodiment of the invention, the mirror 11 can be brought into two predetermined positions 15 and 15' by means of a lever which is connected to a return spring 17. In position 15, which can be adjusted by means of a micrometer screw 16, only reflected light falls on the detector 8 and is measured by means of a measuring instrument 9. In position 15', on the other hand, only the light scattered at a certain angle falls on the detector 8. The ratio of the amounts of light recorded in positions 15 and 15' is a measure of the light diffusion of the specimen.

We claim:

1. A goniophotometer for determining the gloss and/or haze of surfaces, comprising a light source, one or more convex lenses for illuminating the surface, a field stop in the image plane of the light source, and a light detector, wherein a rotatably mounted mirror is located between said surface and said field stop.

2. A goniophotometer as claimed in claim 1, wherein the mirror can be moved by a motor, especially a scanner motor or stepping motor.

* * * * *